United States Patent
Yonezawa et al.

(10) Patent No.: US 6,452,048 B2
(45) Date of Patent: Sep. 17, 2002

(54) PROCESS FOR PRODUCING SULFONYLIMIDE COMPOUND

(75) Inventors: Tetsuo Yonezawa; Yoshitaka Sakamoto, both of Osaka (JP)

(73) Assignee: Morita Chemical Industries Co., Ltd., Osaka (JP)

( * ) Notice: Subject to any disclaimer, the term of this patent is extended or adjusted under 35 U.S.C. 154(b) by 0 days.

(21) Appl. No.: 09/773,648

(22) Filed: Jan. 31, 2001

(30) Foreign Application Priority Data

Jan. 31, 2000 (JP) ........................................ 2000-021578
Jan. 17, 2001 (JP) ........................................ 2001-008448

(51) Int. Cl.$^7$ ............................................ C07C 303/00
(52) U.S. Cl. ........................................ 564/82; 564/80
(58) Field of Search ................................ 564/82, 83, 80

(56) References Cited

U.S. PATENT DOCUMENTS 5,256,821 A * 10/1993 Armand ........................ 564/82
5,874,616 A * 2/1999 Howells et al. ............... 564/82

* cited by examiner

*Primary Examiner*—Samuel Barts
*Assistant Examiner*—Elvis O. Price
(74) *Attorney, Agent, or Firm*—Koda & Androlia

(57) ABSTRACT

A process for producing sulfonylimide compound is represented by the formula (I) $MN(SO_2R_f^1)(SO_2R_f^2)$ industrially easily at a low cost in an efficient manner comprising reactions of at least one sulfonyl halogenides represented by the formula (II) $R_fSO_2X$ with anhydrous ammonia or an ammonium salt in the presence of a fluorine compound represented by the formula (III) MF, in which X represents either F or Cl among halogen elements of VIIb group in the periodic table, and M represents any one of Li, Na, K and Cs among alkali metals of group Ia in the periodic table, $R_f^1$ and $R_f^2$, which may be the same or different, respectively represent any one of a straight chain or branched compound of a fluoroalkyl, perfluoroalkyl, fluoroallyl or fluoroalkenyl group having 1 to 12 carbon atoms, and $R_f$ in the formula (II) represents the same group as $R_f^1$ or $R_f^2$ in the formula (I).

3 Claims, No Drawings

PROCESS FOR PRODUCING SULFONYLIMIDE COMPOUND

BACKGROUND OF THE INVENTION

1. Technical Field of the Invention

The present invention relates to a process for producing a sulfonylimide compound represented by the formula:

$$MN(SO_2R_f^1)(SO_2R_f^2)$$

2. Description of Prior Art

Sulfonylimide compounds are safe as a solute of a battery electrolyte and battery electrolyte that uses the sulfonylimide compound as a solute has a high energy density and exhibits high conductivity. Hence, the sulfonylimide compounds are regarded as a promising solute of a battery electrolyte. Also, the sulfonylimide compounds are useful as a Lewis acid catalyst and an ionic conduction agent.

The sulfonylimide compounds represented by the formula (I) $MN(SO_2R_f^1)(SO_2R_f^2)$ may be synthesized by the process proposed by D. D. Desmarteau et al. in INORGANIC CHEMISTORY VOL. 23, No. 23, P3720–3723 (1984).

In this synthetic method, as shown by the following formula, trifluoromethylsulfonyl fluoride is reacted with ammonium, the resulting product is treated using hydrochloric acid to produce trifluoromethylsulfonylamide, which is then reacted with sodium methylate and then with hexamethyldisilazane, and the resulting product is reacted with trifluoromethylsulfonyl fluoride, thus obtaining an imide sodium salt.

Reaction Formula 1

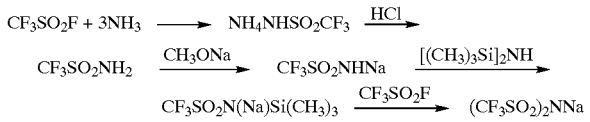

However, this process involves multi-reaction steps and hence takes longer. Also, expensive hexamethyldisilazane must be used to obtain an intermediate, and the yield is as low as about 50%.

In the above-described formula (I), M represents any one of Li, Na, K and Cs among alkali metals of group Ia in the periodic table. $R_f^1$ and $R_f^2$, which may be the same or different, respectively represent any one of a straight chain or branched compound of a fluoroalkyl, perfluoroalkyl, fluoroallyl and fluoroalkenyl group having 1 to 12 carbon atoms (the same hereafter).

In the Japanese Patent Application National Publication No. Hei3-501860, a method is disclosed in which a silazane metal compound is reacted with a perfluorosulfonyl halide compound to obtain an imide compound. In the Japanese Patent Application National Publication No. Hei4-501118, a method is disclosed in which an ionic nitride is reacted with a halogenated sulfonic acid to obtain in imide compound.

However, the silazane metal compound and the ionic nitride used in each of the above prior art are expensive, and hence the above methods are not an economical production method.

Also, in the Japanese Patent Application Laid-Open (Kokai) No. Hei8-81436, a method is disclosed in which anhydrous ammonia or a sulfonylamide and a sulfonyl fluoride are reacted with a tertiary amine or a heterocyclic amine, and the reaction product is further reacted with, for instance, a hydroxide containing an alkali metal and an alkali earth metal to produce imide salts.

In this method, because the product in the first stage is generated as an amine salt, it must be further reacted with an inorganic salt. Also, since a tertiary amine or a heterocyclic amine is used in the reaction, problems concerning work environment caused by the odor and disposal of the amine occur. Moreover, because the anhydrous ammonia is always used, an autoclave as the reactor and a low temperature cooling unit are required. This method is, therefore, unsuitable for mass-production.

As outlined above, the prior art involves a long reaction step and uses expensive raw materials, and it is hence hard to say that these methods in prior art are industrially acceptable methods.

In the Japanese Patent Application Laid-Open (Kokai) No. Hei8-81436, anhydrous ammonia, a perfluoroalkylsulfonyl fluoride and a tertiary amine are reacted with each other. To obtain an imide salt, at least two steps are required; and in the reaction, a tertiary amine or a heterocyclic amine is used, causing possibility of pollution of work environment derived from the odor and the like. Further, the product must be reacted with an alkali metal or the like in an aqueous solution in the second step, and at this time, it is necessary to dispose the amine which is freed and distilled together with water, causing increased production costs.

SUMMARY OF THE INVENTION

It is an object of the present invention to solve these various problems and to produce a sulfonylimide compound industrially easily at a low cost in an efficient manner.

The inventors of the present application have made earnest studies to accomplish the above object and as a result found that a sulfonylimide compound (represented by the formula (I) $MN(SO_2R_f^1)(SO_2R_f^2)$) which is free from the foregoing problems can be produced industrially easily at a low cost in an efficient manner.

More specifically, the present invention comprises a reaction of at least one of the sulfonyl halogenides represented by the formula (II) $R_fSO_2X$ with anhydrous ammonium or an ammonium salt in the presence of fluorine compounds represented by the formula (III) MF.

In the above-described formulas (I) and (II), M represents any one of Li, Na, K and Cs among alkali metals of group Ia in the periodic table, and X represents either F or Cl among halogen elements of VIIb group in the periodic table. Also, $R_f$ in the above-described formula (II) represents the same or identical group as $R_f^1$ or $R_f^2$ in the formula (I).

The inventors have also found that sulfonylimide compound represented by the formula (I) $MN(SO_2R_f^1)(SO_2R_f^2)$ can be produced in the mild conditions that anhydrous ammonium is not always used and in only one-step reaction by reacting a sulfonylamide represented by the formula (IV) $R_fSO_2NH_2$, at least one of the sulfonyl halogenides represented by the formula (II) $R_fSO_2X$, and fluorine compound represented by the formula (III)MF with each other.

Li, Na, K, Rb, Cs and Fr exist as the alkali metals of Ia group in the periodic table. Among these metals, especially any one of Li, Na, K and Cs is selected and used. Therefore, in the case of these metals, the fluorine compounds that are used are LiF, NaF, KF (as KF, any one of calcine-dried KF (cd KF) and spray-dried KF (sd KF) produced by a spray drying method may be used) and CsF The reason why Li, Na, K, and Cs are preferred among alkali metals of group Ia in the periodic table is that they are relatively cheap and suitable to produce sulfonylimide compounds industrially easily, at a low cost and in an efficient manner. Especially, K is prominent for the above property among Li, Na, K, and Cs.

In the present invention, on the other hand, the sulfonylimide compound can be produced by using an ammonium salt. As the ammonium salt in this case, it is desirable to use ammonium fluoride or ammonium hydrogendifluoride. These of either one of these compounds has the advantage that a specific reactor (autoclave) is not required.

$CF_3SO_2Cl$ among sulfonyl halogenides represented by the formula (II) $R_fSO_2X$, which is sold on the market as a reagent, can be usually handled as liquid because its boiling point is 30° C., relatively high among these kinds of compounds.

Although "sulfonylimide" and "sulfonylamide" in the present specification should be expressed formally as "sulfonimide" and "sulfonamide", respectively, both are handled as the same significance.

DETAILED DESCRIPTION OF THE PREFERRED EMBODIMENTS

The embodiment of the present invention will be hereinafter explained in detail.

The object compounds which has been produced in multi-steps in the prior art can be produced in one step by introducing a fluorine compound represented by the formula (III) MF, at least one of the sulfonyl halogenides represented by the formula (II) $R_fSO_2X$, and anhydrous ammonia or an ammonium salt into an inert solvent and reacting the mixture as shown by the following formula 2, 3, 4, and 5.

This is due to the basicity of the fluorine compound represented by the formula (III) MF.

(1) In the case where $R_f^1$ and $R_f^2$ in the formula (I) $MN(SO_2R_f^1)(SO_2R_f^2)$ are the same or equal to each other:

Reaction Formula 2

$$NH_3 + 2R_fSO_2X + 6M \longrightarrow MN(SO_2R_f)_2 + 3MFHF + 2MX$$

One mol of anhydrous ammonium, 2 mol of at least one of the sulfonyl halogenides represented by the formula (II) $R_fSO_2X$ and 6 mol of a fluorine compound represented by the formula (III) MF are introduced into a reactor and the mixture is reacted in a solvent.

After completion of the reaction, 2 mol of the by-produced MX and 3 moles of hydrogendifluoride salt MFHF are removed by filtration, and the filtrate is concentrated. The sulfonylimide compound represented by the formula (I) $MN(SO_2R_f)_2$ can be thereby produced.

(2) In the case where $R_f^1$ and $R_f^2$ in the formula (I) $MN(SO_2R_f^1)(SO_2R_f^2)$ are different from each other:

A sulfonylamide containing the $R_f^1$ group which is produced by a known process shown below is reacted with at least one of the sulfonyl halogenides having a desired $R_f^2$ group. A sulfonylimide compound with the $R_f^1$ group and the $R_f^2$ group are respectively constituted of an objective group can be thereby produced.

Reaction Formula 3

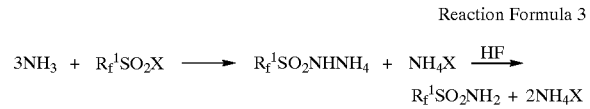

-continued

Reaction Formula 4

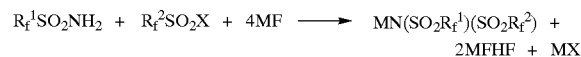

(3) In the case of using an ammonium salt:

Reaction Formula 5

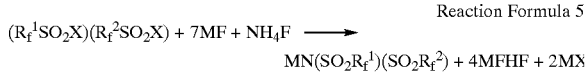

wherein $R_f^1$ and $R_f^2$ are the same or different.

One mol of an ammonium salt, 2 mol of at least one of the sulfonyl halogenides represented by the formula (II) $R_fSO_2X$ and 7 mol of a fluorine compound represented by the formula (III) MF are introduced into a reactor, and the mixture is reacted in a solvent.

After completion of the reaction, 2 mol of the by-produced MX and 4 mol of the by-produced hydrogendifluoride MFHF are removed by filtration, and then the filtrate is concentrated. The sulfonylimide compound represented by the formula (I) $MN(SO_2R_f^1)(SO_2R_f^2)$ can be thereby produced.

These reactions can occur in a temperature range between about −30° C. and 200° C. At a temperature less than this range, the reaction rate is very low whereas at the temperature exceeding the above range, decomposition of the compounds, solvent and product to be used arises. A more preferable temperature range for the reactions is between 0° C. and 100° C.

As to the solvent, any solvent can be used without particular limitations as far as it is inert to the reaction materials. For example, ethers such as diethyl ether and tetrahydrofuran, halogenated hydrocarbons such as dichloromethane and dichloroethane, hydrocarbons such as benzene, heptane and hexane and nitrites such as acetonitrile can be used.

In order to produce various sulfonylimide compounds other than those described above, a sulfonylimide compound obtained by these production methods is made into an acid by using concentrated sulfuric acid and the acid is distilled to thereby synthesize a sulfonylimidic acid $[HN(SO_2R_f^1)(SO_2R_f^2)]$. This acid can be further reacted with a compound selected from hydroxides, oxides, carbonates and acetates of metals corresponding to this acid.

In this case, fluorine compounds represented by the formula (III) MF to be used in the synthesis of a sulfonylimide compound can be compounded and used.

EXAMPLES

The present invention will be described in more detail by way of examples, which, of course, do not limit the present invention.

Example 1

A flask with four necks was charged with 150 ml of acetonitrile, 23.4 g of potassium fluoride and 20 g of trifluoromethylsulfonylamide $CF_3SO_2NH_2$. The reactor was soaked in a 40° C. hot water bath, and 25.1 g of trifluoromethylsulfonyl fluoride $CF_3SO_2F$ was introduced with sufficient stirring. The reaction solution was subjected to filtration, and the filtrate was concentrated under reduced pressure to obtain potassium bistrifluoromethylsulfonylimide $KN(SO_2CF_3)_2$ in an amount of 42.7 g. The yield was 99%.

Next, 42.7 g of this potassium bistrifluoromethylsulfonylimide was added in a flask that was charged with 60 ml of concentrated sulfuric acid, and the mixture was dissolved under heat. Under reduced pressure, 34.6 g of bistrifluoromethylsulfonylimidic acid $HN(SO_2CF_3)_2$ was distilled by distillation. The yield was 92%.

Then, 34.6 g of the resulting bistrifluoromethylsulfonylimidic acid was dissolved in pure water and reacted with 4.5 g of lithium carbonate. Excess lithium carbonate was removed by filtration, and the filtrate was concentrated to obtain 34.6 g of lithium bistrifluoromethylsulfonylimide $LiN(SO_2CF_3)_2$. The yield was 98%.

Example 2

An autoclave made of stainless was charged with 200 ml of acetonitrile and 68.3 g of potassium fluoride. The reactor was cooled to −60° C. in a dry ice/methanol bath, and 5 g of anhydrous ammonia was introduced.

In succession, 90.0 g of trifluoromethylsulfonyl fluoride $CF_3SO_2F$ was introduced, and the temperature of the mixture was returned to ambient temperature with sufficient stirring. After that, the reactor was soaked in a 40° C. hot water bath, and the reaction was completed while stirring sufficiently. The reaction solution was subjected to filtration, and the filtrate was concentrated under reduced pressure to obtain 88.2 g of potassium bistrifluoromethylsulfonylimide $KN(SO_2CF_3)_2$. The yield was 95%.

Example 3

A flask with four necks was charged with 1 liter of methylene chloride, 10 g of ammonium fluoride and 78.4 g of potassium fluoride. The reactor was soaked in a 40° C. hot water bath, and 82.1 g of trifluoromethylsulfonyl fluoride $CF_3SO_2F$ was introduced while stirring sufficiently. The reaction solution was subjected to filtration, and the filtrate was concentrated under reduced pressure to obtain 81.5 g of potassium bistrifluoromethylsulfonylimide $KN(SO_2CF_3)_2$. The yield was 95%.

Example 4

A flask was charged with 300 ml of DMF (dimethylformamide), 30 g of perfluorobutylsulfonyl fluoride $C_4F_9SO_2F$, 15.1 g of trifluoromethylsulfonylamide $CF_3SO_2NH_2$ and 13 g of sodium fluoride, and the mixture was heated to 100° C. and sufficiently stirred to react. The reaction solution was subjected to filtration, and the filtrate was concentrated under reduced pressure to obtain 35.1 g of sodium perfluorobutylsulfonyl-trifluoromethylsulfonylimide $NaN(SO_2C_4F_9)(SO_2CF_3)$. The yield was 78.0%.

Example 5

A flask with four necks was charged with 200 ml of acetonitrile, 12 g of perfluorobuthylsulfonyl fluoride $C_4F_9SO_2F$, 15.0 g of cesium fluoride, and 0.73 g of ammonium fluoride, and the mixture was heated 50° C. and sufficiently stirred to react. The reaction solution was subjected to filtration, and the filtrate was concentrated under reduced pressure to obtain 12.5 g of cesium bisperfluorobuthylsulfonylimide $CsN(SO_2C_4F_9)_2$. The yield was 89.3%.

Example 6

An autoclave made of stainless was charged with 100 ml of dichloromethane, 100 ml of DMF (dimethylformamide) and 30.5 g of lithium fluoride. The reactor was cooled to −60° C. in a dry ice/ methanol bath, and 5 g of anhydrous ammonia was introduced.

In succession, 100.0 g of trifluoromethylsulfonyl floride $CF_3SO_2F$ was introduced, and the temperature of the mixture was returned to ambient temperature with sufficient stirring. After that, the reactor was soaked in a 50° C. hot water bath, and the reaction was run while stirring sufficiently.

The reaction solution was subjected to filtration, and the filtrate was concentrated under reduced pressure, but only 1.7 g of lithium bistrifluoromethylsulfonylimide $LiN(SO_2CF_3)_2$ was obtained (the yield was 2.0%).

Although the amount and percentage yield of the product compound in this case were lower than in the case of other examples, this case is expected to be improved by further studies. Such an improved case should be indeed in the scope of the present invention.

Example 7

A flask with four necks was charged with 150 ml of acetonitrile, 31.2 g of potassium fluoride, and 10 g of trifluoromethylsulfonylamide $CF_3SO_2NH_2$ were added. The reactor was soaked in a 40° C. water bath, and 11.3 g of trifluoromethylsulfonyl chloride $CF_3SO_2Cl$ was introduced while stirring sufficiently. The reaction solution was subjected to filtration, and the filtrate was concentrated under reduced pressure to obtain 21.4 g of potassium bistrifluoromethylsulfonylimide $KN(SO_2CF_3)_2$. The yield was 96%.

In succession, 21.4 g of potassium bistrifluoromethylsulfonylimide was added in a flask that was charged with 30 ml of concentrated sulfuric acid, and the mixture was dissolved under heat. And then, 15.6 g of bistrifluoromethylsulfonylimidic acid $HN(SO_2CF_3)_2$ was distilled by distillation under reduced pressure. The yield was 83%.

The resulting 15.6 g of bistrifluoromethylsulfonylimidic acid was dissolved in the pure water and reacted with 2.1 g of lithium carbonate. Excess lithium carbonate was subjected to filtration, and the filtrate was concentrated to obtain 15.4 g of lithium bistrifluoromethylsulfonylimide $LiN(SO_2CF_3)_2$. The yield was 97%.

Example 8

A flask with four necks was charged with 200 ml of methylene chloride, 10 g of ammonium fluoride, and 110 g of potassium fluoride. The reactor was soaked in a 40° C. water bath, and 91.0 g of trifluoromethylsulfonyl chloride $CF_3SO_2Cl$ was introduced while stirring sufficiently. The reaction solution was subjected to filtration, and the filtrate was concentrated under reduced pressure to obtain 81.0 g of potassium bistrifluoromethylsulfonylimide $KN(SO_2CF_3)_2$. The yield was 94%.

Example 9

A flask with four necks was charged with 5 g of ammonium fluoride, 143.6 g of cesium fluoride, and 200 ml of tetrahydrofuran. With sufficiently stirring the reactor, 22.8 g of trifluoromethylsulfonyl chloride $CF_3SO_2Cl$ was introduced, and then 27.3 g of pentafluoroethylsulfonyl fluoride $C_2F_5SO_2F$ was added. The reaction solution was treated in the same way as Example 2 to obtain 62 g of cesium perfluoroethylsulfonyl trifluoromethylsulfonylimide $CsN(SO_2C_2F_5)(SO_2CF_3)$. The yield was 99.2%.

Example 10

In a SUS (stainless)-made autoclave, 200 ml of methylene chloride, 300 ml of DMF (dimethylformamide), 45.6 g of lithium fluoride, and 99.0 g of trifluoromethylsulfonyl chloride $CF_3SO_2Cl$ were added. The reactor was cooled to −60° C. in a methanol/dry ice bath, and 5 g of anhydrous ammonia was introduced.

The reaction mixture was returned to the room temperature while stirring sufficiently, and then the reactor was soaked in a 80° C. water bath, and the reaction was run while stirring sufficiently. Consequently, the reaction solution was treated in the same way as Example 2, but only 0.8 g of lithium bistrifluoromethylsulfonylimide $LiN(SO_2CF_3)_2$ was obtained (the yield was 0.9%). The amount and yield of the product were considerably lower than the cases of other Examples, however, further improvement may be expected by the future investigations. This invention naturally includes such a case.

Example 11

In a SUS (stainless)-made autoclave, 200 ml of methylene chloride, 300 ml of DMF (dimethylformamide), 74.1 g of sodium fluoride, and 49.5 g of trifluoromethylsulfonyl chloride $CF_3SO_2Cl$ were added. The reactor was cooled to −60° C. in a methanol/dry ice bath, and 5 g of anhydrous ammonia was introduced.

Consequently, 88.8 g of perfluorobuthylsulfonyl fluoride $C_4F_9SO_2F$ was added, and the reaction mixture was returned to the room temperature with stirring sufficiently. And then, the reactor was soaked in a 80° C. water bath, and the reaction was run while stirring sufficiently. Consequently, the reaction solution was treated in the same way as Example 2, to obtain 18 g of sodium perfluorobuthylsulfonyl trifluoromethylsulfonylimide $NaN(SO_2C_4F_9)(SO_2CF_3)$. The yield was 13.5%.

It should be noted that the sulfonylimide compounds obtained in the above examples were respectively confirmed by identifying them using an infrared absorption spectrum.

As seen from the above description, the production process of the present invention has such an effect that sulfonylimide compounds useful as lithium battery electrolytes and organic synthetic catalysts are produced industrially easily at a low cost in an efficient manner.

Furthermore, the production process according to the present invention has such an effect that by reacting a sulfonylamide, a sulfonyl fluoride and a fluorine compound with each other, a sulfonylimide compound useful as lithium battery electrolytes and organic synthtic catalysts is produced under a mild condition that anhydrous ammonia is not always used, and in one stage. Also, a specific reactor (autoclave) is not required unlike the case that uses anhydrous ammonia.

What is claimed is:

1. A process for producing a sulfonylimide compound represented by the formula (I):

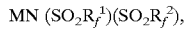

wherein M represents any one of Li, Na, K and Cs among alkali metals of group Ia in the periodic table, $R_f^1$ and $R_f^2$, which are the same or different and respectively represent any one of a straight chain or branched compound of a fluoroalkyl, perfluoroaklyl, fluoroallyl or fluoroalkenyl group having 1 to 12 carbon atoms, wherein the process comprises the single step of reacting:

at least one of sulfonyl halogenides represented by the formula (II): $R_fSO_2X$, wherein $R_f$ represents the same or identical group as $R_f^1$ or $R_f^2$ in the formula (I), and X represents either F or Cl among halogen elements of VIIb group in the periodic table, anhydrous ammonia or an ammonium salt, and a fluorine compound represented by the Formula (II): MF, wherein M represents any one of Li, Na, K and Cs among alkali metals of group Ia in the periodic table together.

2. A process for producing a sulfonylimide compound represented by the formula (I):

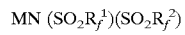

wherein M represents any one of Li, Na, K and Cs among alkali metals of group Ia in the periodic table, $R_f^1$ and $R_f^2$, which are the same or different and respectively represent any one of a straight chain or branched compound of a fluoroalkyl, perfluoroaklyl, fluoroallyl or fluoroalkenyl group having 1 to 12 carbon atoms, wherein the process comprises the single step of reacting:

a sulfonylamide represented by the formula (IV): $R_fSO_2NH_2$, wherein $R_f$ represents the same group as $R_f^1$ or $R_f^2$ in the formula (I), at least one of sulfonyl halogenides represented by the formula (II): $R_fSO_2X$, wherein $R_f$ represents the same or identical group as $R_f^1$ or $R_f^2$ in the formula (I), and X represents either F or Cl among halogen elements of VIIb group in the element periodic table, and a fluorine compound represented by the formula (III): MF, wherein M represents any one of Li, Na, K and Cs among alkali metals of group Ia in the periodic table together.

3. The process for producing a sulfonylimide compound according to claim 1, wherein an ammonium fluoride or an ammonium hydrogendifluoride is used as the ammonium salt.

* * * * *

UNITED STATES PATENT AND TRADEMARK OFFICE
CERTIFICATE OF CORRECTION

PATENT NO.      : 6,452,048 B2
DATED           : September 17, 2002
INVENTOR(S)     : Tetsuo Yonezawa et al.

It is certified that error appears in the above-identified patent and that said Letters Patent is hereby corrected as shown below:

<u>Column 8,</u>
Line 17, change "Formula (II) : MF" to -- Formula (III) : MF --

Signed and Sealed this

Fifth Day of August, 2003

JAMES E. ROGAN
*Director of the United States Patent and Trademark Office*